(12) United States Patent
Nakamura et al.

(10) Patent No.: US 12,365,850 B2
(45) Date of Patent: *Jul. 22, 2025

(54) WATER-MISCIBLE FUNCTIONAL FLUID, UNDILUTED STOCK OF WATER-MISCIBLE FUNCTIONAL FLUID, STERILIZER FOR WATER-MISCIBLE FUNCTIONAL FLUID, AND METHOD OF STERILIZING WATER-MISCIBLE FUNCTION FLUID

(71) Applicant: YUSHIRO CHEMICAL INDUSTRY CO., LTD., Tokyo (JP)

(72) Inventors: Genta Nakamura, Kanagawa (JP); Yasumasa Ohashi, Kanagawa (JP)

(73) Assignee: Yushiro Chemical Industry Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/926,025

(22) PCT Filed: Apr. 26, 2021

(86) PCT No.: PCT/JP2021/016649
§ 371 (c)(1),
(2) Date: Nov. 17, 2022

(87) PCT Pub. No.: WO2021/235187
PCT Pub. Date: Nov. 25, 2021

(65) Prior Publication Data
US 2023/0174889 A1 Jun. 8, 2023

(30) Foreign Application Priority Data

May 22, 2020 (JP) ................................. 2020-089454

(51) Int. Cl.
*C10M 173/00* (2006.01)
*A61L 2/08* (2006.01)
(Continued)

(52) U.S. Cl.
CPC ........... *C10M 173/00* (2013.01); *A61L 2/088* (2013.01); *A61L 2101/44* (2020.08);
(Continued)

(58) Field of Classification Search
CPC .............. C10M 173/02; C10M 173/00; C10M 2201/062; C10M 2215/221;
(Continued)

(56) References Cited

U.S. PATENT DOCUMENTS 5,780,860 A * 7/1998 Gadgil ...................... A61L 2/10
250/435
2003/0073650 A1 4/2003 Reddy et al.
(Continued)

FOREIGN PATENT DOCUMENTS

JP 61-40720 B2 9/1986
JP 63-245494 A 10/1988
(Continued)

OTHER PUBLICATIONS

International Search Report for PCT/JP2021/016649 dated Jun. 1, 2021.

*Primary Examiner* — Vishal V Vasisth
(74) *Attorney, Agent, or Firm* — Sughrue Mion, PLLC (57) ABSTRACT

A water-miscible functional fluid includes: a neutral photosensitizer having an isoalloxazine skeleton; and an antioxidant, wherein the antioxidant is a radical scavenger or a peroxide decomposer.

12 Claims, 3 Drawing Sheets

(51) Int. Cl.
*A61L 101/44* (2006.01)
*C10N 20/00* (2006.01)
*C10N 30/10* (2006.01)
*C10N 30/16* (2006.01)
*C10N 40/22* (2006.01)

(52) U.S. Cl.
CPC ... *C10M 2203/06* (2013.01); *C10N 2020/091* (2020.05); *C10N 2030/10* (2013.01); *C10N 2030/16* (2013.01); *C10N 2040/22* (2013.01)

(58) Field of Classification Search
CPC .... C10M 2215/042; C10M 2203/1006; C10M 2203/06; C10M 2223/04; C10M 2219/044; C10M 2207/02; C10M 2215/224; C10M 2207/125; C10M 2207/026; A61L 2/088; A61L 2/08; A61L 2101/00; A61L 2101/44
See application file for complete search history.

(56) References Cited

U.S. PATENT DOCUMENTS

| 2009/0220647 A1 | 9/2009 | Shinozaki et al. |
| 2016/0088853 A1 | 3/2016 | Tikekar et al. |

FOREIGN PATENT DOCUMENTS

| JP | 2-29496 A | | 1/1990 |
| JP | 2-212597 A | | 8/1990 |
| JP | 4-264199 A | | 9/1992 |
| JP | 2004-018444 A | | 1/2004 |
| JP | 2004-500316 A | | 1/2004 |
| JP | 2006-087563 A | | 4/2006 |
| JP | 2009073932 A | * | 4/2009 |
| JP | 2009-161585 A | | 7/2009 |
| JP | 2016084285 A | * | 5/2016 |
| WO | 2006/132353 A1 | | 12/2006 |

* cited by examiner

WATER-MISCIBLE FUNCTIONAL FLUID, UNDILUTED STOCK OF WATER-MISCIBLE FUNCTIONAL FLUID, STERILIZER FOR WATER-MISCIBLE FUNCTIONAL FLUID, AND METHOD OF STERILIZING WATER-MISCIBLE FUNCTION FLUID

CROSS REFERENCE TO RELATED APPLICATIONS

This application is a National Stage of International Application No. PCT/JP2021/016649 filed Apr. 26, 2021, claiming priority based on Japanese Patent Application No. 2020-089454 filed May 22, 2020, the entire contents of which are hereby incorporated by reference.

TECHNICAL FIELD

The present disclosure relates to a water-miscible functional fluid, an undiluted stock of the water-miscible functional fluid, a sterilizer for a water-miscible functional fluid, and a method of sterilizing a water-miscible functional fluid.

BACKGROUND ART

Metalworking fluids are used for lubrication and/or cooling between a working tool and a workpiece in metalworking such as cutting, grinding, and plastic working. Metalworking fluids as used herein include an oil-based metalworking fluid and a water-miscible metalworking fluid. A water-miscible metalworking fluid is mainly used because such a fluid can lead to efficient cooling, and fire prevention in processing even with an automated machine. A large amount of a metalworking fluid is used in metalworking as being circulated by a pump.

A water-miscible metalworking fluid for metalworking is generally produced by appropriately mixing a mineral oil, a fat and an oil, a fatty acid, a fatty acid ester, an extreme pressure additive, a surfactant, an antifoaming agent, a metal corrosion inhibitor, an antioxidant, a preservative and an antifungal agent, etc. according to the purpose. The produced water-miscible metalworking fluid is diluted with water to be a so-called coolant for use. A primary performance relating to a cutting ability, grindability, etc., and a secondary performance relating to workability etc. are required of the coolant. Examples of the primary performance include to improve the precision on a finished surface, and to extend a tool life. Examples of the secondary performance include to be highly rust-resistant, to be difficult to deteriorate and easy to manage, to be harmless to humans, and to be less foaming.

A water-miscible metalworking fluid contains a lot of substances as described above which are nutrient sources for microorganisms including bacteria, yeast, and mold. Thus, a coolant obtained after a water-miscible metalworking fluid is diluted is putrescible, which is problematic. Progress of this putrefaction causes both the primary and secondary performances to decline. Moreover, the putrefaction causes odor, which is also problematic. If the putrefaction increases the frequency of a change of metalworking fluids, a water-miscible metalworking fluid is also at a cost disadvantage. Furthermore, a molded coolant also causes a pipe in a circulation system including a pump to clog. To prevent them, metalworking fluids are subjected to preservative and antifungal treatment by adding a preservative and an antifungal agent, or with any other component.

Generally, however, the effects of preservatives and antifungal agents considerably lessen in a short time due to decomposition or inactivation thereof, which is problematic. Examples of widely known preservatives and antifungal agents include formaldehyde releasing type, and phenolic preservatives and antifungal agents, which are irritants. In other words, when such a preservative and an antifungal agent are added to a metalworking fluid in such a large amount that the metalworking fluid becomes antiputrefactive and/or fungus-resistant, the metalworking fluid itself becomes a severe skin irritant, and may adversely affect the human body.

There is a metalworking fluid using an amine soap as a surfactant (emulsifier): the amine soap is obtained by reacting a fatty acid and any amine (Patent Literature 1). In this case, a free alkaline amine is present in the metalworking fluid. A metalworking fluid containing such a free amine a lot can be antiputrefactive and/or fungus-resistant to some extent. There is also a technique of containing an antibacterial amine in a metalworking fluid (Patent Literature 2). Or, a technique of making the pH of a metalworking fluid high (making the alkalinity thereof a pH of 9 or more) to secure antiputrefactive properties is also known.

The following are known in this field as techniques of using no preservative or amine: electromagnetic radiation (Patent Literatures 3 and 4); ultrasound radiation (Patent Literature 5); ozone sterilization (Patent Literature 6); and UV sterilization (Patent Literature 7) which are each known as a method of sterilizing a metalworking fluid or a coolant physicochemically or in terms of a device.

CITATION LIST

Patent Literature

Patent Literature 1: JP S61-40720 B2
Patent Literature 2: JP 2009-161585 A
Patent Literature 3: JP H2-212597 A
Patent Literature 4: JP H2-29496 A
Patent Literature 5: JP S63-245494 A
Patent Literature 6: JP 2006-087563 A
Patent Literature 7: JP H4-264199 A
Patent Literature 8: JP 2004-018444 A

SUMMARY OF INVENTION

Technical Problem

A lot of a free amine is necessary when an antiputrefactive effect is sufficiently exerted by, for example, adding the free amine to a metalworking fluid; therefore, a technique more effective against putrefaction has been required. A negative impact on the global environment and the human body is concerned when antiputrefactive effect is exerted by adding an antibacterial amine because the antibacterial amine may have a biotoxicity. When the pH is made to be high to secure antiputrefactive properties, occurrence of severe dermal disorders is concerned; and metal corrosion is also concerned when a nonferrous metal is processed.

The method using an electromagnetic wave or an ultrasonic wave may lead to any change in properties of metalworking fluid components in a coolant, or destruction of an emulsion.

The method using ozone may lead to degradation of a function as a metalworking fluid because the oxidizing power of the generated ozone is so strong as to destroy coolant components; moreover, may lead to deterioration of a working environment due to strong corrosivity and toxicity of the generated ozone, which makes it necessary to take measures against corrosion etc. on equipment, and to take measures such as installation and management of an abatement system conforming to work environment standards etc.

UV irradiation sterilization is sterilization by damaging DNA of microorganisms, and thus, is effective for all bacterial species. Moreover, a method using such sterilization has many advantages such as no fear of destruction of coolant components, and no resistant bacteria produced. However, an ultraviolet ray has a peak wavelength of 400 nm or shorter, which is short and is inferior in transmittance. Therefore, as shown in Patent Literature 7, it is necessary to provide such a shallow portion in a circulation path of a coolant that the coolant can be sufficiently irradiated with an ultraviolet ray. It is also essential to take measures such as (personal protective) equipment for limiting exposure of workers during the irradiation.

As described above, UV sterilization is a sterilization method using the fact that DNA of organisms is damaged by ultraviolet rays. However, almost all organisms have some repair functions against DNA damage caused by ultraviolet rays. One of the functions is called "photoreactivation", which is a phenomenon that when irradiated with light within near-ultraviolet and visible regions, a microorganism inactivated by UV irradiation repairs DNA thereof to be reactivated using the action of a photoreactivating enzyme thereof. The mechanism of this phenomenon is introduced in, for example, "YAMAMOTO, Enzymatic Photoreactivation. SEIBUTSU BUTSURI (1985), Vol. 25, No. 3". Like this, UV sterilization is not considered to be preferable for the purpose of permanently sterilizing a fluid circulating in a device.

The above-described sterilization methods require introduction of a large-scale facility such as an electromagnetic wave generator, an ozonizer, and a UV light generator; and the costs of the facility and operation mount up, which is problematic. Further, an antiputrefactive effect corresponding to these costs is not considered to be obtained.

Hereinafter a "singlet oxygen generation photosterilization method" that has hardly been considered as a physicochemical sterilization method in a conventional metalworking fluid field will be described.

This is a sterilization method using a photosensitizer. The method is as follows: a triplet state photosensitizer has excitation energy substantially equal to the energy difference between singlet oxygen and triplet oxygen; thus, a photosensitizer is made to be photoexcited by visible light to be transitioned into an excited triplet state via intersystem crossing; a collision of the photosensitizer in this state with triplet oxygen causes electrons and energy to be exchanged, so that the photosensitizer returns to the ground state, and at the same time, the triplet oxygen transitions to singlet oxygen; and using such a mechanism, singlet oxygen is generated by light irradiation, and then, sterilization is performed by the strong oxidative effect of the singlet oxygen. This method was discovered in the early twentieth century as photodynamic therapy (PDT), and is still widely used in medical and hygienic fields at present. This sterilization method allows visible light irradiation to lead to the reaction because using a photosensitizer. Thus, a risk to workers from exposure can be avoided unlike any sterilization method using UV irradiation. In addition, this method can solve the problems with physicochemical sterilization methods and methods in terms of a device as described above because in this method, a photosensitizer is added to a metalworking fluid, and this metalworking fluid is irradiated with visible light.

Various compounds such as synthetic dyes including rose bengal and methylene blue, and riboflavin compounds that are biocomponents harmless to humans are known as compounds offering photosensitization.

Patent Literature 8 shows a transfused blood bactericidal method of irradiating a riboflavin compound that is a biocomponent harmless to humans with visible light: the riboflavin compound is used here as a photosensitizer. However, it is difficult to obtain practical sterilizability by addition of a riboflavin compound to an ordinary metalworking fluid because this addition causes various problems attended with oxidation of components, such as a pH drop, which is a cause of rust.

An object of the present disclosure is to provide an antibacterial and antiputrefactive water-miscible functional fluid that utilizes photosterilization: the water-miscible functional fluid can keep being antibacterial for a long time, has less odor and skin irritation, and further, is safe, and is excellent in fluid stability.

Solution to Problem

As a result of their intensive study to solve the above problems, the inventors of the present invention obtained the following findings.

Antiputrefactive properties of a conventional water-miscible functional fluid depend on a preservative, or a lot of an antibacterial free amine. There has been no practically antiputrefactive water-miscible functional fluid unless such a preservative or a free amine is contained therein. A photosterilization method of adding a photosensitizer is effective as a method of sterilizing a water-miscible functional fluid without depending on a preservative or a free amine at no huge costs of installation, management, etc. of a new machine.

Then, addition of a riboflavin compound as a photosensitizer was tried. As a result, separation or precipitation, or photoinactivation, or the like did not occur; and the sterilizing power was maintained. However, the problem of a significant pH drop was clarified, which is a cause of trouble with a water-miscible functional fluid, such as rust generation.

The present invention was made based on the above findings, and is as follows.

<1>

A water-miscible functional fluid comprising: a neutral photosensitizer having an isoalloxazine skeleton; and an antioxidant, wherein the antioxidant is a radical scavenger or a peroxide decomposer.

<2>

The water-miscible functional fluid according to <1> to be used as a water-miscible cutting fluid, a water-miscible grinding fluid, a water-miscible detergent, a water-miscible stamping fluid, a water-miscible forging fluid, a water-miscible rolling fluid, a water-miscible release agent, a water-miscible sawing fluid, a water-miscible polishing fluid, or a water-miscible hydraulic fluid.

<3>

An undiluted stock of the water-miscible functional fluid according to <1> or <2>, the undiluted stock comprising: a neutral photosensitizer having an isoalloxazine skeleton; and an antioxidant, wherein the antioxidant is a radical scavenger or a peroxide decomposer.

<4>

The undiluted stock according to <3> to be used as an undiluted stock of a water-miscible cutting fluid, a water-miscible grinding fluid, a water-miscible detergent, a water-miscible stamping fluid, a water-miscible forging fluid, a water-miscible rolling fluid, a water-miscible release agent, a water-miscible sawing fluid, a water-miscible polishing fluid, or a water-miscible hydraulic fluid.

<5>

A sterilizer adapted to sterilize the water-miscible functional fluid according to <1> or <2>, the sterilizer comprising: a storing part in which at least the water-miscible functional fluid is stored; a light irradiation part with which the water-miscible functional fluid is irradiated with light: a metal-working machine with which metalworking is performed with the water-miscible functional fluid; and a circulation part via which the water-miscible functional fluid is circulated around the storing part and the metal-working machine, wherein the water-miscible functional fluid sterilized with the light irradiation part is supplied to the metal-working machine via the circulation part.

<6>

The sterilizer according to <5>, wherein the light irradiation part is installed in the storing part.

<7>

The sterilizer according to <5>, wherein the light irradiation part is installed outside the storing part.

<8>

A method of sterilizing a water-miscible functional fluid, the method comprising:

irradiating the water-miscible functional fluid according to <1> or <2> with visible light having a wavelength in a range of 380 nm to 500 nm.

Advantageous Effects of Invention

The present disclosure can offer an antibacterial and antiputrefactive water-miscible functional fluid that utilizes photosterilization: the water-miscible functional fluid can keep being antibacterial for a long time, has less odor and skin irritation, and further, is safe, and is excellent in fluid stability.

DESCRIPTION OF EMBODIMENTS

1. Water-miscible Functional Fluid

A water-miscible functional fluid according to the present disclosure contains a neutral photosensitizer having an isoalloxazine skeleton, and an antioxidant.

1.1. Neutral Photosensitizer

A neutral photosensitizer as used in the present disclosure has an isoalloxazine skeleton represented by the following formula (1):

(1)

In the formula (1), $R^1$ to $R^5$ is each a H1-3 or C1-3 hydrocarbon group, for example, a methyl group. $R^1$ to $R^5$ may be the same as or different from each other.

In the formula (1), $R^6$ is a H1-10 or C1-10 hydrocarbon group. Examples of a substituent in the hydrocarbon group include a hydroxyl group, an ester, and a phosphate ester.

$R^6$ may be derived from a sugar alcohol.

In the present disclosure, the neutral photosensitizer having molecules in a triplet state has excitation energy substantially equal to the energy difference between singlet oxygen ($^1O_2$) and triplet oxygen ($^3O_2$). Thus, the neutral photosensitizer is made to be photoexcited by visible light to be transitioned into an excited triplet state via intersystem crossing. A collision of the neutral photosensitizer in this excited triplet state with $^3O_2$ causes electrons and energy to be exchanged, so that the neutral photosensitizer returns to the ground state, and at the same time, $^3O_2$ transitions to $^1O_2$. Using such a mechanism, sterilization is performed by the strong sterilizability of the singlet oxygen ($^1O_2$).

In the present disclosure, specific examples of the neutral photosensitizer include the following compounds.

[Lumichrome] (Following Formula (2))

(2)

[Riboflavin] (Following Formula (3))

(3)

[Riboflavin Butyrate] (Following Formula (4))

[Riboflavin Sodium Phosphate] (Following Formula (5))

Preferably 20 ppm to 1000 ppm of the neutral photosensitizer is added to the water-miscible functional fluid according to the present disclosure based on 100 parts by weight total water-miscible functional fluid. Here, ppm represents a weight ratio. At least 20 ppm of the neutral photosensitizer can lead to effective photo-sterilizability. At most 1000 ppm of the neutral photosensitizer leads to sufficient photo-sterilizability, and also can prevent equipment fouling to lead to an economically preferred water-miscible functional fluid.

1.2. Antioxidant

The water-miscible functional fluid according to the present disclosure contains an antioxidant for suppressing a pH drop.

In a photosensitizing reaction, a neutral photosensitizer having an isoalloxazine skeleton is made to be photoexcited to react with oxygen molecules to generate singlet oxygen as described above. In addition, the photoexcited neutral photosensitizer causes metalworking fluid components to generate a radical via a homolytic hydrogen atom abstraction reaction. The radical reacts with oxygen to form a peroxy radical or a peroxide. Further, a hydroxyl radical that is a strong oxidant is generated from the peroxide to oxidize the metalworking fluid components. It is considered that the metalworking fluid components are oxidized by this chain reaction to generate an acidic compound such as a carboxylic acid, which decrease the pH. A pH drop in the water-miscible functional fluid causes metal corrosion on processing machinery and workpieces, and therefore, has to be suppressed.

Examples of the added antioxidant include radical scavengers and peroxide decomposers.

Examples of phenolic radical scavengers among the radical scavengers include D-α-tocopherol, butylated hydroxytoluene (BHT), Irganox® 1010 (from BASF JAPAN, Ltd.), Irganox® 1076 (from BASF JAPAN, Ltd.), Irganox® 1330 (from BASF JAPAN, Ltd.), Irganox® 3114 (from BASF JAPAN, Ltd.), Irganox® 3125 (from Ciba Specialty Chemicals), Irganox® 3790 (from Ciba Specialty Chemicals), Cyanox® 1790 (from Cyanamid), and Sumilizer® GA-80 (from SUMITOMO CHEMICAL COMPANY, LIMITED). An example of ascorbic acid based radical scavengers among the radical scavengers is sodium ascorbate.

Examples of phosphorus-based peroxide decomposers among the peroxide decomposers include tris(1,1,1,3,3,3-hexafluoro-2-propyl)phosphite, triphenyl phosphite, triisodecyl phosphite, tributyl phosphite, tris(2,4-di-tert-butylphenyl) phosphite, tris(2-methylphenyl) phosphite, tris(4-methylphenyl) phosphite, tris(2-ethylhexyl)phosphite, and pentaerythritol bis(2,4-di-tert-butylphenylphosphite).

An example of sulfur-based peroxide decomposers among the peroxide decomposers is 2-mercaptobenzimidazole. Examples of organic sulfur compounds among the sulfur-based peroxide decomposers include commercially available products such as DSTP [Yoshitomi]® (from Yoshitomiyakuhin Corporation), DLTP [Yoshitomi]® (from Yoshitomiyakuhin Corporation), DLTOIB® (from Yoshitomiyakuhin Corporation), DMTP [Yoshitomi]® (from Yoshitomiyakuhin Corporation), Seenox412S® (from SHIPRO KASEI KAISHA, LTD.), and Cyanox® 1212 (from Cyanamid).

Examples of amine-based peroxide decomposers among the peroxide decomposers include monoethanol amine, monoisopropanolamine, diethanolamine, di-isopropanolamine, triethanolamine, triisopropanolamine, 1,3-Bis (aminomethyl)cyclohexane, N,N'-Di-sec-butyl-1,4-phenylenediamine, disodium edetate, Irgastab® FS 042 (from Ciba Specialty Chemicals), GENOX® EP (from Crompton, compound name: dialkyl-N-methylamine oxide), and hindered amine based peroxide decomposers such as ADK STAB LA-52, LA-57, LA-62, LA-63, LA-67, LA-68, LA-77, LA-82, LA-87 and LA-94 manufactured by ADEKA Corporation, Tinuvin 123, 144, 440 and 662, and Chimassorb 2020, 119 and 944 manufactured by CSC, Hostavin N30 manufactured by Hoechst, Cyasorb UV-3346 and UV-3526 manufactured by Cytec, Uval 299 manufactured by GLC, and Sanduvor PR-31 manufactured by Clariant.

Preferably 0.0001 parts by weight to 0.03 parts by weight of the antioxidant is added based on 100 parts by weight total water-miscible functional fluid.

1.3. Others

[Rust Inhibitor]

The water-miscible functional fluid according to the present disclosure may contain a rust inhibitor that is contained in a conventional water-miscible functional fluid. Examples of the rust inhibitor include alkanolamines, potassium hydroxide, sodium hydroxide, carboxylates, phosphates, polyphosphates, tungstates, molybdates, and sulfonates.

[Emulsifying Substance]

The water-miscible functional fluid according to the present disclosure may contain a mineral oil or an ester or both of them as an emulsifying substance.

Examples of the mineral oil include paraffinic or naphthenic mineral oils obtained by refining lubricant oil fractions that are obtained by distillation of crude oil under atmospheric pressure and under reduced pressure, through refining processes such as solvent deasphalting, solvent extraction, hydrocracking, solvent dewaxing, catalytic dewaxing, hydrorefining, sulfuric acid washing, and white clay treatment in appropriate combination.

Examples of the ester include condensates of a carboxylic acid and an alcohol such as 2-ethylhexanol, trimethylolpropane, pentaerythritol, neopentyl glycol erythritol, glycerin, and sorbitol.

The content of the emulsifying substance is not particularly limited. Preferably, 0.25 parts by weight to 6.0 parts by weight of the emulsifying substance is contained based on 100 parts by weight total functional fluid. At least 0.25 parts by weight of the added emulsifying substance can secure lubricity. At most 6.0 parts by weight of the added emulsifying substance leads to sufficient lubricity, and also can prevent emulsion stability from being undermined to lead to an economically preferred water-miscible functional fluid.

[Surfactant]

Preferably, an emulsion-type water-miscible functional fluid further contains a surfactant. As the surfactant, any of anionic surfactants, nonionic surfactants, and the like that are conventionally used for water-miscible metalworking fluids may be arbitrarily selected and used.

Examples of the anionic surfactants include fatty acid amine salts, and fatty acid metal salts (such as potassium and sodium).

Examples of the nonionic surfactants include polyoxyalkylene alkyl ether such as polyoxyethylene alkyl ether, and polyoxyethylene polyoxypropylene alkyl ether, polyethylene glycol polypropylene glycol blocked polymers, coconut fatty acid diethanolamide, oleic acid diethanolamide, and fatty acid monoesters or diesters of polyalkylene glycol.

The content of the surfactant is not particularly limited. Preferably, 0.5 parts by weight to 3.5 parts by weight of the surfactant is contained based on 100 parts by weight total functional fluid. At least 0.5 parts by weight of the added surfactant can lead to formation of good emulsion. At most 3.5 parts by weight of the added surfactant can prevent trouble for foaming to lead to an economically preferred water-miscible functional fluid.

2. Use of Water-miscible Functional Fluid

The water-miscible functional fluid according to the present disclosure may be used as a water-miscible cutting fluid, a water-miscible grinding fluid, a water-miscible detergent, a water-miscible stamping fluid, a water-miscible forging fluid, a water-miscible rolling fluid, a water-miscible sawing fluid, a water-miscible polishing fluid, a water-miscible hydraulic fluid, or a water-miscible release agent.

3. Undiluted Stock of Water-miscible Functional Fluid

An undiluted stock of a water-miscible functional fluid according to the present disclosure is provided with the above-described components of the water-miscible functional fluid at a concentration 5 to 100 times those in the water-miscible functional fluid.

In view of transportability, handleability, etc., the water-miscible functional fluid is on the market in the form of an undiluted stock that is a concentrate. Therefore, a user who purchased the concentrate dilutes the undiluted stock five to hundred-fold with water so that the concentration of a basic photosensitizer is at most 5 ppm, and then, uses the diluted stock as the water-miscible functional fluid.

In view of lubricity at a processing point (concentration of the emulsifying substance), the undiluted stock is preferably five to fifty-fold diluted, more preferably ten to thirty-fold diluted, and most preferably twenty-fold diluted.

The undiluted stock of the water-miscible functional fluid may contain the neutral photosensitizer having an isoalloxazine skeleton in a range of 100 ppm to 10000 ppm, and the antioxidant in a range of 0.1 parts by weight to 5 parts by weight, based on 100 parts by weight total undiluted stock.

The undiluted stock of the water-miscible functional fluid may contain the emulsifying substance in a range of 50 parts by weight to 80 parts by weight, and the surfactant in a range of 10 parts by weight to 70 parts by weight, on the basis of the total amount of the undiluted stock.

4. Sterilizer Adapted to Water-miscible Functional Fluid

Figure 1:
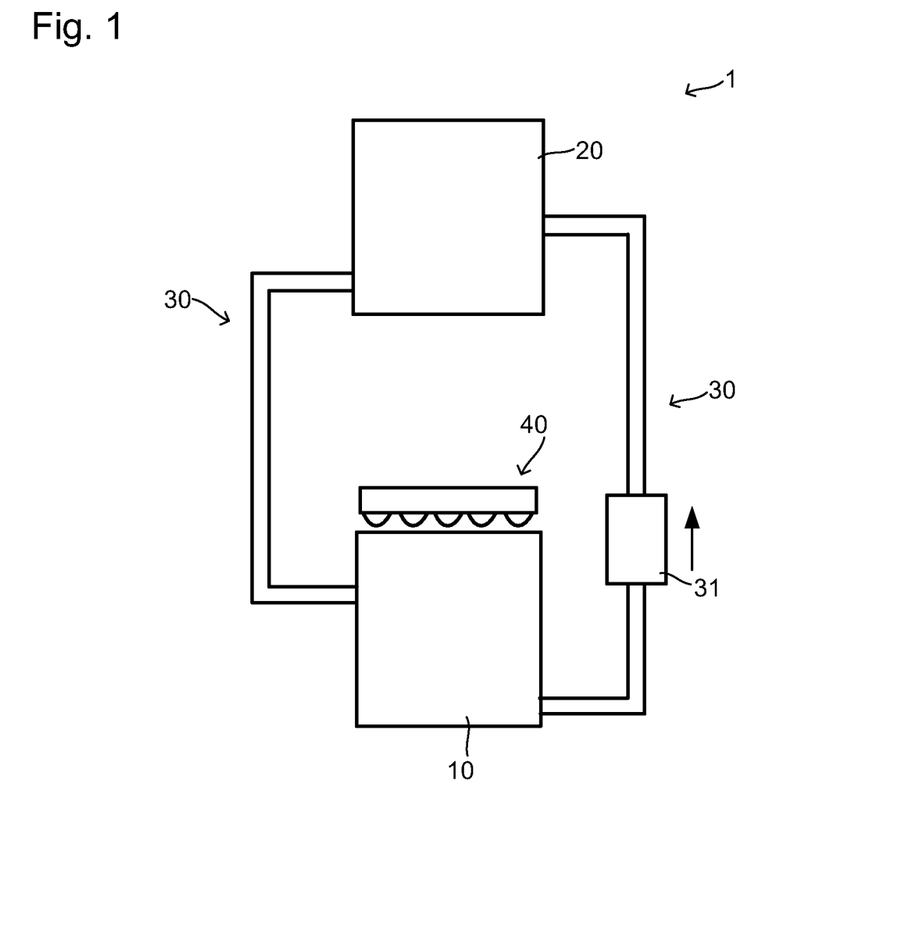
FIG. 1 is a schematic view illustrating structure of a sterilizer 1.

As shown in FIG. 1, a sterilizer 1 adapted to a water-miscible functional fluid according to the present disclosure is provided with: a storing part (tank) 10 adapted to store at least a water-miscible functional fluid; a metal-working machine 20 installed at at least one place with which metal is processed using the water-miscible functional fluid; a circulation part 30 that is piping via which the water-miscible functional fluid is supplied to the metal-working machine, and via which the water-miscible functional fluid used in the metal-working machine is collected and returned to the storing part again; and a light irradiation part 40 that is a light irradiator for irradiating the water-miscible functional fluid with light from an LED light source to photo-sterilize the water-miscible functional fluid. The water-miscible functional fluid sterilized with the light irradiation part is circulated around the storing part and the metal-working machine via the circulation part, and is supplied to the metal-working machine. A filter for removing scraps etc. that were generated during the processing and are included in the collected water-miscible functional fluid may be further provided.

The water-miscible functional fluid stored in the storing part (tank) 10 is circulated around the storing part (tank) 10 and the metal-working machine 20 (via the circulation part 30) by a pump 31, and irradiation of the functional fluid with light in a visible region at the light irradiation part 40 sterilizes the functional fluid to kill microorganisms generated during the storage, the circulation, or the use in the metal-working machine, such as bacteria, yeast, and mold. This leads to storage of the water-miscible functional fluid having less microorganisms in the storing part 10.

The sterilizer 1 according to the present disclosure may be appropriately modified according to the scale, the mode, etc. of the equipment as long as having at least the above structure. For example, the light irradiation part 40 may be installed in the storing part 10 adapted to store the water-miscible functional fluid, or may be installed outside the storing part, for example, in the piping, which is the circulation part 30, or in a purifier installed on part of the piping. This sterilizer 1 is installed for the purpose of sterilizing the water-miscible functional fluid to be used in the metal-working machine 20. Thus, preferably, the structure of the sterilizer 1 conforms to "JIS B 6016-2 Machine tools-Lubrication systems".

5. Method of Sterilizing Water-miscible Functional Fluid

The water-miscible functional fluid according to the present disclosure can be sterilized by irradiation with light in a visible region at the light irradiation part.

Specifically, a method of irradiation with light from an LED as a light source is used. An LED having a dominant wavelength (strongest wavelength) in a range of 380 nm to 500 nm is preferable.

A discharge lamp such as a metal halide lamp, a high-pressure mercury lamp, a xenon lamp, a halogen lamp, and a pulsed xenon lamp may be used. The light of this lamp may be passed through an optical filter to be adjusted to have the above preferred wavelength.

The irradiation way is not particularly limited. For example, irradiation with light having an irradiance of 1 µW/cm$^2$ to 1500 µW/cm$^2$ may be performed. The irradiance is preferably at least 100 µW/cm$^2$, and may be at least 1200 µW/cm$^2$. The irradiation may be performed so that the cumulative light intensity is 10 J/cm$^2$ to 500 J/cm$^2$. The cumulative light intensity is preferably 30 J/cm$^2$ to 400 J/cm$^2$, and more preferably 100 J/cm$^2$ to 400 J/cm$^2$.

EXAMPLES

[Sterilizability of Neutral Photosensitizer Having Isoalloxazine Skeleton]

A water-miscible functional fluid (YUSHIRON FORMER® ER53 manufactured by YUSHIRO CHEMICAL INDUSTRY CO., LTD.,) collected from practical facilities was adjusted to have a predetermined concentration, and added to autoclaved Hutsu-buiyon-baichi (normal broth medium) (Eiken® manufactured by EIKEN CHEMICAL CO., LTD.) to be cultured under shaking with a shaker at 120 rpm at 30° C. for 24 hours. The resultant fluid that had a bacterial count reaching approximately 1.0×10$^9$ CFU/ml was used as a bacterial suspension for inoculation. This bacterial suspension was diluted with autoclaved physiological saline solution so as to be adjusted to have a bacterial count of 1.4×10$^7$ CFU/ml. The prepared suspension was used as a test solution.

Bacteria was counted with a serial dilution method: the bacterial count was calculated by counting colonies appeared after 4-hour stationary culture on a nutrient agar medium at 30° C.

Figure 2:
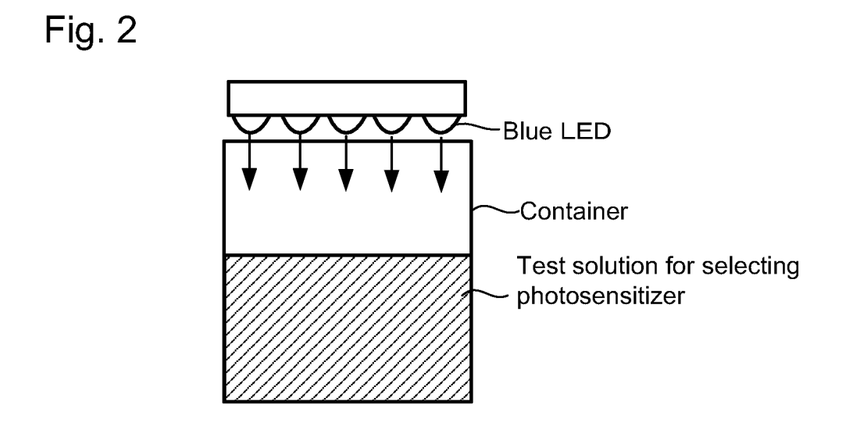
FIG. 2 schematically shows a device for a photosterilization test.

Each neutral photosensitizer shown in table 1 in an amount shown in table 1 was added to the above test solution, to prepare a test solution for selecting a photosensitizer. In a container, 100 mL of this prepared test solution was put and irradiated with light from thirty blue LEDs (OSB56A5111A manufactured by OptoSupply Limited, bullet type LED (5 mm), wavelength: 475 nm) as stirred with a stirrer: the LEDs were arranged at a place apart from the level of the test solution as shown in FIG. 2 so that a predetermined irradiance could be given on the level. After 30 minutes had passed, the bacterial count in each of the test solutions was confirmed by the following criteria:

++: bacterial count was 1.0×10$^6$ CFU/ml to 1.4×10$^7$ CFU/ml

+: bacterial count was at least 1.0×10$^2$ CFU/ml and less than 1.0×10$^6$ CFU/ml −: bacterial count was at least 0 and less than 1.0×10$^2$ CFU/mil

TABLE 1

| | Photosensitizer | | Irradiation light | | Bacterial count | | | | | |
|---|---|---|---|---|---|---|---|---|---|---|
| | Type | Amount added (ppm) | Wavelength (nm) | Irradiance (µW/cm2) | Light intensity (J/cm2) | | | | | |
| | | | | | 10 | 30 | 50 | 100 | 200 | 400 |
| Comparative example 1 | None | — | 380 | 1200 | ++ | ++ | ++ | ++ | ++ | ++ |
| Comparative example 2 | None | — | 275 | 100 | ++ | ++ | ++ | ++ | + | + |
| Example 1 | Riboflavin | 50 | 500 | 100 | ++ | ++ | ++ | ++ | + | + |
| Example 2 | Lumichrome | 20 | 450 | 100 | ++ | + | − | − | − | − |
| Example 3 | Riboflavin | 50 | 450 | 100 | ++ | + | + | + | − | − |
| Example 4 | Riboflavin | 50 | 380 | 1200 | ++ | ++ | ++ | + | + | + |
| Example 5 | Riboflavin | 50 | 275 | 100 | ++ | ++ | + | + | + | − |
| Example 6 | Riboflavin sodium phosphate | 50 | 450 | 100 | ++ | + | + | + | − | − |
| Example 7 | Riboflavin butyrate | 50 | 450 | 100 | ++ | + | + | + | − | − |

In comparative example 1, where no photosensitizer was added, no change in the bacterial count due to the light irradiation was found. In comparative example 2, however, a decrease in the bacterial count was found when the cumulative light intensity was increased. This is considered to be because the sterilizability of the light itself was shown since the wavelength of the irradiation light was short and was an ultraviolet ray in a UVC region which has strong sterilizing power.

In contrast, in example 1, a decrease in the bacterial count was found at places where the light intensity was higher although the wavelength of the irradiation light was 500 nm, which was longer than the comparative examples and was in such a range that irradiation with light having a wavelength in this range is not sufficient for sterilization. Accordingly, the present disclosure can lead to exertion of sterilizability of irradiation even with light having such a less dangerous wavelength in a visible light region. Further, the light transmittivity can be improved since it is not necessary to shorten the wavelength of the irradiation light unlike that in comparative example 2.

In all examples 2 to 7, a decrease in the bacterial count was found, and an effect to a greater degree than the UV sterilization shown in comparative example 2 was confirmed.

[pH Drop Suppression]

Next, a test on pH drop suppression using an antioxidant will be described.

Figure 3:
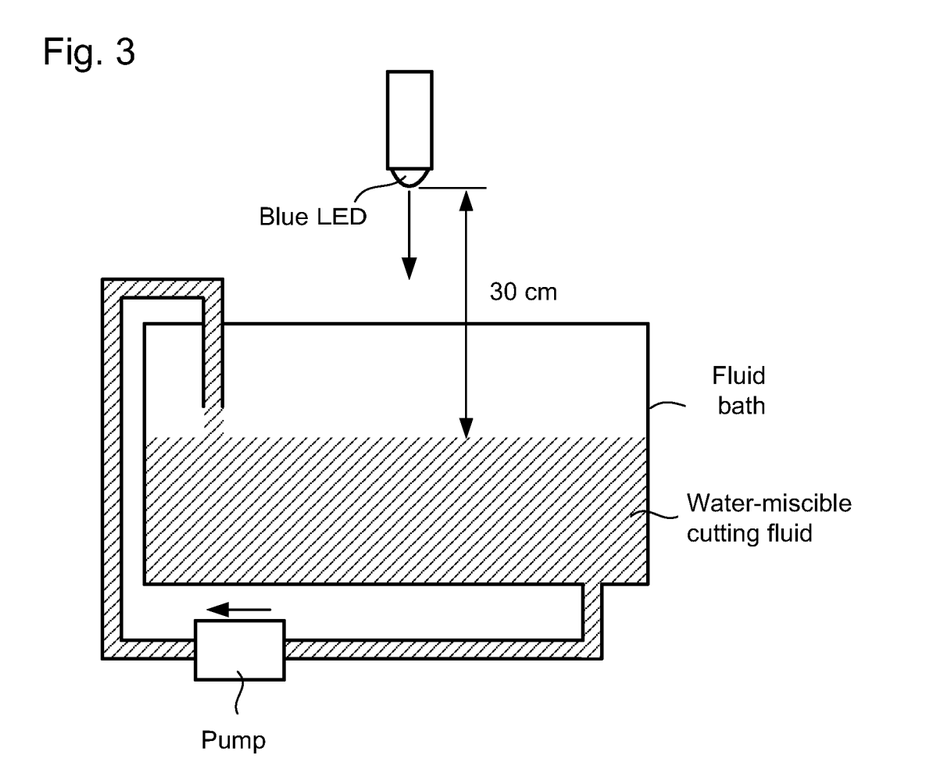
FIG. 3 schematically shows a device for photosterilization and pH drop suppression test.

An undiluted stock of each example which contained the components shown in table 2 was diluted with water so as to be a 5% diluted solution, to prepare 2000 g of a water-miscible cutting fluid. This cutting fluid was put in a fluid bath having a volume of 5 L as shown in FIG. 3, and this diluted solution was adjusted with hydrochloric acid so that an initial pH thereof was 8.6±0.1, and thereafter, circulated by a pump. Further, 200 g of cuttings of a casting were added to this water-miscible cutting fluid and circulated by a pump. At the same time, the fluid was continuously irradiated with light from a blue LED (TRI-450 manufactured by NDT Advance inc.) that was at a place apart from the fluid level by 30 cm. For confirming sterilizability, on each of the first and the third days of the test, 100 ml of an inoculate for a test (bacteria: $1.0\times10^7$ CFU/ml, mold: $1.0\times10^3$ CFU/ml, and yeast: $1.0\times10^3$ CFU/ml) was added: the inoculate was prepared by culturing a water-miscible functional fluid Yushiroken® FX1000 collected from practical facilities. For measuring the bacterial count, "Sani-Check BF" (manufactured by Biosan Laboratories, Inc.) was used.

Table 2 shows the components of the undiluted stock, and the test result (evaluations) of each example.

The pH was adjusted so as to be 8.6±0.1 in advance as described above. In relation to this, the pH value after one-month continuous circulation by the pump and irradiation with the light from the blue LED was also shown. The difference between pHs before and after this test was also shown as a pH change.

Concerning the photo-sterilizability, the bacterial count, the mold count, and the yeast count one week after the start of the test were measured with "Sani-Check BF" (manufactured by Biosan Laboratories, Inc.) and evaluated based on the following criteria.

<Bacteria>
 o: at least 0 and less than $1.0\times10^5$ CFU/ml
 x: at least $1.0\times10^5$ CFU/ml <Mold and Yeast>
 o: at least 0 and less than $1.0\times10^2$ CFU/ml
 x: at least $1.0\times10^2$ CFU/ml When the water-miscible cutting fluid prepared with the components of the undiluted stock of example 11 was not irradiated with light, the bacterial count was $1.0\times10^7$ CFU/ml, the mold count was $1.0\times10^2$ CFU/ml, and the yeast count was $1.0\times10^2$ CFU/ml.

TABLE 2

| | | | | | Comparative example | Examples | | | | | |
|---|---|---|---|---|---|---|---|---|---|---|---|
| | | | | | 11 | 11 | 12 | 13 | 14 | 15 | 16 |
| Components of undiluted stock | Oleic acid | | | | 0.5 | 0.5 | 0.5 | 0.5 | 0.5 | 0.5 | 0.5 |
| | 5(or 6)-carboxy-4-hexylcyclohex-2-ene-1-octanoic acid | | | | 2.5 | 2.5 | 2.5 | 2.5 | 2.5 | 2.5 | 2.5 |
| | Synthetic Ester | | | | 4 | 1 | 1 | 1 | 1 | 1 | 1 |
| | Sodium petroleum sulphonate | | | | 5 | 5 | 5 | 5 | 5 | 5 | 5 |
| | Potassium hydroxide (50% aqueous solution) | | | | 1.5 | 1.5 | 1.5 | 1.5 | 1.5 | 1.5 | 1.5 |
| | C14 alcohol | | | | 3 | 3 | 3 | 3 | 3 | 3 | 3 |
| | Mineral oil | | | | 73.9 | 71.9 | 73.85 | 73.4 | 73.4 | 73.4 | 73.7 |
| | Nonionic surfactant | | | | 8 | 11 | 11 | 11 | 11 | 11 | 11 |
| | Riboflavin (neutral photosensitizer) | | | | 0.1 | 0.1 | 0.1 | 0.1 | 0.1 | 0.1 | 0.1 |
| | Water | | | | 1.5 | 1.5 | 1.5 | 1.5 | 1.5 | 1.5 | 1.5 |
| | Antioxidant | Radical scavenger | Hindered phenolic | D-α-tocopherol | — | 2 | — | — | — | — | — |
| | | | | BHT | — | — | 0.05 | — | — | — | — |
| | | | | Irqanox 1010 | — | — | — | 0.5 | — | — | — |
| | | | | Irqanox 3114 | — | — | — | — | 0.5 | — | — |
| | | | Ascorbic acid based | Sodium ascorbate | — | — | — | — | — | 0.5 | — |
| | | Peroxide decomposer | Phosphorus-based | Tris(2,4-di-tert-butylphenyl) Phosphate | — | — | — | — | — | — | 0.2 |
| | | | | Tributyl phosphite | — | — | — | — | — | — | — |
| | | | Sulfur-based | 2-mercaptobenzimidazole | — | — | — | — | — | — | — |
| | | | Amine-based | Monoethanol amine | — | — | — | — | — | — | — |
| | | | | Monoisopropanolamine | — | — | — | — | — | — | — |
| | | | | Diethanolamine | — | — | — | — | — | — | — |
| | | | | Di-isopropanolamine | — | — | — | — | — | — | — |
| | | | | Triethanolamine | — | — | — | — | — | — | — |
| | | | | Triisopropanolamine | — | — | — | — | — | — | — |
| | | | | 1,3-BBis(aminomethyl)cyclohexane | — | — | — | — | — | — | — |
| | | | | N,N'-Di-sec-butyl-1,4-phenylenediamine | — | — | — | — | — | — | — |
| | | | | Disodium edetate (EDTA-2Na) | — | — | — | — | — | — | — |
| | | Singlet oxygen decomposer | | Sodium azide | — | — | — | — | — | — | — |
| | Total | | | | 100 | 100 | 100 | 100 | 100 | 100 | 100 |
| Evaluation | pH | | | pH at time of preparation (5% diluted solution) | 8.5 | 8.6 | 8.6 | 8.6 | 8.6 | 8.6 | 8.6 |
| | | | | pH after continuous use (one month) | 5.9 | 8.0 | 7.6 | 8.1 | 7.8 | 6.5 | 8.2 |
| | | | | pH change | 2.6 | 0.6 | 1.0 | 0.5 | 0.8 | 2.1 | 0.4 |
| | Photo- | | | Bacteria | o | o | o | o | o | o | o |

TABLE 2-continued

Unit for components of undiluted stock: weight %

| | | | | | Examples | | | | | | |
|---|---|---|---|---|---|---|---|---|---|---|---|
| | | | | | 17 | 18 | 19 | 20 | 21 | 22 | 23 |
| | sterilizability | | Yeast | | ○ | ○ | ○ | ○ | ○ | ○ | ○ |
| | | | Mold | | ○ | ○ | ○ | ○ | ○ | ○ | ○ |

| | | | | | | 17 | 18 | 19 | 20 | 21 | 22 | 23 |
|---|---|---|---|---|---|---|---|---|---|---|---|---|
| Components of undiluted stock | Oleic acid | | | | | 0.5 | 0.5 | 0.5 | 0.5 | 0.5 | 0.5 | 0.5 |
| | 5(or 6)-carboxy-4-hexylcyclohex-2-ene-1-octanoic acid | | | | | 2.5 | 2.5 | 2.5 | 2.5 | 2.5 | 2.5 | 2.5 |
| | Synthetic Ester | | | | | 1 | 1 | 1 | 1 | 1 | 1 | 1 |
| | Sodium petroleum sulphonate | | | | | 5 | 5 | 5 | 5 | 5 | 5 | 5 |
| | Potassium hydroxide (50% aqueous solution) | | | | | 1.5 | 1.5 | 1.7 | 1.5 | 1.5 | 1.5 | 1.5 |
| | C14 alcohol | | | | | 3 | 3 | 3 | 3 | 3 | 3 | 3 |
| | Mineral oil | | | | | 73.4 | 72.9 | 72.9 | 72.9 | 72.9 | 72.9 | 72.9 |
| | Nonionic surfactant | | | | | 11 | 11 | 11 | 11 | 11 | 11 | 11 |
| | Riboflavin (neutral photosensitizer) | | | | | 0.1 | 0.1 | 0.1 | 0.1 | 0.1 | 0.1 | 0.1 |
| | Water | | | | | 1.5 | 1.5 | 1.5 | 1.5 | 1.5 | 1.5 | 1.5 |
| | Antioxidant | Radical scavenger | Hindered phenolic | D-α-tocopherol | | — | — | — | — | — | — | — |
| | | | | BHT | | — | — | — | — | — | — | — |
| | | | | Irqanox 1010 | | — | — | — | — | — | — | — |
| | | | | Irqanox 3114 | | — | — | — | — | — | — | — |
| | | | Ascorbic acid based | Sodium ascorbate | | — | — | — | — | — | — | — |
| | | Peroxide decomposer | Phosphorus-based | Tris(2,4-di-tert-butylphenyl) Phosphate | | — | — | — | — | — | — | — |
| | | | | Tributyl phosphite | | 0.5 | — | — | — | — | — | — |
| | | | Sulfur-based | 2-mercaptobenzimidazole | | — | 1 | — | — | — | — | — |
| | | | Amine-based | Monoethanol amine | | — | — | 1 | — | — | — | — |
| | | | | Monoisopropanolamine | | — | — | — | 1 | — | — | — |
| | | | | Diethanolamine | | — | — | — | — | 1 | — | — |
| | | | | Di-isopropanolamine | | — | — | — | — | — | 1 | — |
| | | | | Triethanolamine | | — | — | — | — | — | — | 1 |
| | | | | Triisopropanolamine | | — | — | — | — | — | — | — |
| | | | | 1,3-BBis(aminomethyl)cyclohexane | | — | — | — | — | — | — | — |
| | | | | N,N'-Di-sec-butyl-1,4-phenylenediamine | | — | — | — | — | — | — | — |
| | | | | Disodium edetate (EDTA-2Na) | | — | — | — | — | — | — | — |
| | | Singlet oxygen decomposer | | Sodium azide | | — | — | — | — | — | — | — |
| Evaluation | Total | | | | | 100 | 100 | 100.2 | 100 | 100 | 100 | 100 |
| | pH | | | pH at time of preparation (5% diluted solution) | | 8.6 | 8.6 | 8.6 | 8.7 | 8.5 | 8.7 | 8.5 |
| | | | | pH after continuous use (one month) | | 8.2 | 6.2 | 7.1 | 7.0 | 7.8 | 8.0 | 7.7 |
| | | | | pH change | | 0.4 | 2.4 | 1.5 | 1.7 | 0.7 | 0.7 | 0.8 |
| | Photo-sterilizability | | | Bacteria | | ○ | ○ | ○ | ○ | ○ | ○ | ○ |
| | | | | Yeast | | ○ | ○ | ○ | ○ | ○ | ○ | ○ |
| | | | | Mold | | ○ | ○ | ○ | ○ | ○ | ○ | ○ |

| | | | | | Examples | | | | | Comparative example |
|---|---|---|---|---|---|---|---|---|---|---|
| | | | | | 24 | 25 | 27 | 28 | 29 | 12 |
| Components of undiluted stock | Oleic acid | | | | 0.5 | 0.5 | 0.5 | 0.5 | 0.5 | 0.5 |
| | 5(or 6)-carboxy-4-hexylcyclohex-2-ene-1-octanoic acid | | | | 2.5 | 2.5 | 2.5 | 2.5 | 2.5 | 2.5 |
| | Synthetic Ester | | | | 1 | 1 | 1 | 1 | 4 | 4 |
| | Sodium petroleum sulphonate | | | | 5 | 5 | 5 | 5 | 5 | 5 |
| | Potassium hydroxide (50% aqueous solution) | | | | 1.5 | 1.5 | 1.5 | 1.5 | 1.5 | 1.5 |
| | C14 alcohol | | | | 3 | 3 | 3 | 3 | 3 | 3 |
| | Mineral oil | | | | 72.9 | 72.9 | 73.4 | 72.8 | 73.9 | 73.9 |
| | Nonionic surfactant | | | | 11 | 11 | 11 | 11 | 8 | 8 |
| | Riboflavin (neutral photosensitizer) | | | | 0.1 | 0.1 | 0.1 | 0.1 | 0.1 | 0.1 |
| | Water | | | | 1.5 | 1.5 | 1.5 | 1.5 | 1.5 | 1.5 |
| | Antioxidant | Radical scavenger | Hindered phenolic | D-α-tocopherol | — | — | — | — | — | — |
| | | | | BHT | — | — | — | — | — | — |
| | | | | Irqanox 1010 | — | — | — | 0.1 | — | — |
| | | | | Irqanox 3114 | — | — | — | — | — | — |

TABLE 2-continued

Unit for components of undiluted stock: weight %

| | | | | | | | | | |
|---|---|---|---|---|---|---|---|---|---|
| | | Peroxide decomposer | Ascorbic acid based | Sodium ascorbate | — | — | — | — | — | — |
| | | | Phosphorus-based | Tris(2,4-di-tert-butylphenyl) Phosphate | — | — | — | — | — | — |
| | | | | Tributyl phosphite | — | — | — | — | — | — |
| | | | Sulfur-based | 2-mercaptobenzimidazole | — | — | — | — | — | — |
| | | | Amine-based | Monoethanol amine | — | — | — | — | — | — |
| | | | | Monoisopropanolamine | — | — | — | — | — | — |
| | | | | Diethanolamine | — | — | — | 1 | — | — |
| | | | | Di-isopropanolamine | — | — | — | — | — | — |
| | | | | Triethanolamine | — | — | — | — | — | — |
| | | | | Triisopropanolamine | 1 | — | — | — | — | — |
| | | | | 1,3-BBis (aminomethyl)cyclohexane | — | 1 | — | — | — | — |
| | | | | N,N'-Di-sec-butyl-1,4-phenylenediamine | — | — | 0.5 | — | — | — |
| | | | | Disodium edetate (EDTA-2Na) | — | — | — | — | 0.5 | — |
| | | Singlet oxygen decomposer | | Sodium azide | — | — | — | — | — | 0.1 |
| | Total | | | | 100 | 100 | 100 | 100 | 100 | 100 |
| Evaluation | pH | | | pH at time of preparation (5% diluted solution) | 8.6 | 8.6 | 8.6 | 8.5 | 8.6 | 8.6 |
| | | | | pH after continuous use (one month) | 7.8 | 7.2 | 8.2 | 8.0 | 7.8 | 5.7 |
| | | | | pH chanqe | 0.8 | 1.4 | 0.4 | 0.5 | 0.8 | 2.9 |
| | Photo-sterilizability | | | Bacteria | ○ | ○ | ○ | ○ | ○ | ○ |
| | | | | Yeast | ○ | ○ | ○ | ○ | ○ | ○ |
| | | | | Mold | ○ | ○ | ○ | ○ | ○ | ○ |

In table 3, the antioxidants and pH drop suppression were focused on and summarized based on the above results. The values of the pH change in table 3 are the same as those in table 2. The pH change rate was calculated by the following formula:

pH change rate=100%×(pH at the time of the preparation−pH after continuing use)/(pH at the time of the preparation)

On the basis of this pH change rate, the cutting fluid having a pH change rate of 15% or lower was defined as A, the cutting fluid having a pH change rate higher than 15% and at most 20% was defined as B, the cutting fluid having a pH change rate higher than 20% and at most 30% was defined as C, and the cutting fluid having a pH change rate higher than 30% was defined as D. As seen from table 3, the pH change rate of the cutting fluid containing no antioxidant was 31.4%.

TABLE 3

| | Antioxidant | | pH change | pH change rate (%) | Evaluation of pH drop supression |
|---|---|---|---|---|---|
| Radical scavenger | Phenolic | D-α-tocopherol | 0.6 | 7.0 | A |
| | | BHT | 1 | 11.6 | A |
| | | Irganox 1010 | 0.5 | 5.8 | A |
| | | Irganox 3114 | 0.8 | 9.3 | A |
| | Ascorbic acid based | Sodium ascorbate | 2.1 | 24.4 | C |
| Peroxide decomposer | Phosphorus-based | Tris(2,4-di-tert-butylphenyl) phosphite | 0.4 | 4.7 | A |
| | | Tributyl phosphite | 0.4 | 4.7 | A |
| | Sulfur-based | 2-mercaptobenzimidazole | 2.4 | 27.9 | C |
| | Amine-based | Monoethanol amine (primary amine) | 1.5 | 17.4 | B |
| | | Monoisopropanolamine (primary amine) | 1.7 | 19.8 | B |
| | | Di-ethanolamine (secondary amine) | 0.7 | 8.1 | A |
| | | Di-isopropanolamine (secondary amine) | 0.7 | 8.1 | A |
| | | Tri-ethanolamine (tertiary amine) | 0.8 | 9.3 | A |
| | | Triiso-propanolamine (tertiary amine) | 0.8 | 9.3 | A |
| | | 1,3-Bis(aminomethyl)cyclohexane (primary amine) | 1.4 | 16.3 | B |
| | | N,N'-Di-sec-butyl-1,4-phenylenediamine (secondary amine) | 0.4 | 4.7 | A |

TABLE 3-continued

| Antioxidant | | pH change | pH change rate (%) | Evaluation of pH drop supression |
|---|---|---|---|---|
| | Disodium edetate (EDTA-2Na) (tertiary amine) | 0.8 | 9.3 | A |
| Singlet oxygen decomposer | Sodium azide | 2.9 | 33.7 | D |
| | No antioxidant | 2.6 | 31.4 | D |

As seen from table 2, the undiluted stocks in all the examples contained riboflavin that is a neutral photosensitizer having an isoalloxazine skeleton, and thus, were excellent in photo-sterilizability. However, in comparative example 11, where no antioxidant was contained, the value of a pH drop after one-month continuous use reached 2.6, and the pH did not reach 6.0.

As seen from tables 2 and 3, the radical scavengers and the peroxide decomposers were found to exert the effect of pH drop suppression among the antioxidants, but a singlet oxygen decomposer (sodium azide) was not found to exert such an effect. From this, it can be also understood that the sterilizability of singlet oxygen ($^1O_2$) is effective.

It can be also understood that phenolic radical scavengers, peroxide decomposers of secondary amines and tertiary amines, and phosphorus-based peroxide decomposers highly exerted, and peroxide decomposers of primary amines second highly exerted the effect of pH drop suppression among the radical scavengers and the peroxide decomposers.

REFERENCE SIGNS LIST 1 sterilizer
10 storing part
20 metal-working machine
30 circulation part
31 pump
40 light irradiation part

What is claimed is:

1. A water-miscible functional fluid comprising:
a neutral photosensitizer having an isoalloxazine skeleton;
an antioxidant;
a rust inhibitor; and
a surfactant, wherein
the neutral photosensitizer is riboflavin sodium phosphate and/or riboflavin butyrate;
the antioxidant is at least one selected from the group consisting of D-α-tocopherol, pentaerythritol tetrakis(3-(3,5-di-tert-butyl-4-hydroxyphenyl)propionate), 1,3,5-Tris(3,5-di-tert-butyl-4-hydroxybenzyl)-1,3,5-triazine-2,4,6(1H,3H,5H)-trione, tris(2,4-di-tert-butylphenyl)phosphite, tributyl phosphite, a secondary amine, and a tertiary amine,
a content of the neutral photosensitizer is 20 ppm to 1000 ppm, and
a content of the antioxidant is 0.0001 parts by weight to 0.03 parts by weight.

2. The water-miscible functional fluid according to claim 1 to be used as a water-miscible cutting fluid, a water-miscible grinding fluid, a water-miscible detergent, a water-miscible stamping fluid, a water-miscible forging fluid, a water-miscible rolling fluid, a water-miscible release agent, a water-miscible sawing fluid, a water-miscible polishing fluid, or a water-miscible hydraulic fluid.

3. An undiluted stock of the water-miscible functional fluid according to claim 1, wherein
a content of the neutral photosensitizer in the undiluted stock is 100 ppm to 10000 ppm, and
a content of the antioxidant in the undiluted stock is 0.1 parts by weight to 5 parts by weight.

4. The undiluted stock according to claim 3 to be used as an undiluted stock of a water-miscible cutting fluid, a water-miscible grinding fluid, a water-miscible detergent, a water-miscible stamping fluid, a water-miscible forging fluid, a water-miscible rolling fluid, a water-miscible release agent, a water-miscible sawing fluid, a water-miscible polishing fluid, or a water-miscible hydraulic fluid.

5. A sterilizer adapted to sterilize the water-miscible functional fluid according to claim 1, the sterilizer comprising:
a storing part in which at least the water-miscible functional fluid is stored;
a light irradiation part with which the water-miscible functional fluid is irradiated with light:
a metal-working machine with which metalworking is performed with the water-miscible functional fluid; and
a circulation part via which the water-miscible functional fluid is circulated around the storing part and the metal-working machine, wherein
the water-miscible functional fluid sterilized with the light irradiation part is supplied to the metal-working machine via the circulation part.

6. The sterilizer according to claim 5, wherein the light irradiation part is installed in the storing part.

7. The sterilizer according to claim 5, wherein the light irradiation part is installed in the circulation part.

8. A method of sterilizing a water-miscible functional fluid, the method comprising:
irradiating the water-miscible functional fluid according to claim 1 with visible light having a wavelength in a range of 380 nm to 500 nm.

9. The water-miscible functional fluid according to claim 1, wherein the antioxidant is a secondary amine selected from the group consisting of diethanolamine and di-isopropanolamine and N,N'-Di-sec-butyl-1,4-phenylenediamine.

10. The water-miscible functional fluid according to claim 1, wherein the antioxidant is a tertiary amine selected from the group consisting of triethanolamine, triisopropanolamine, and disodium edetate.

11. The water-miscible functional fluid according to claim 1, wherein the neutral photosensitizer is riboflavin sodium phosphate.

12. The water-miscible functional fluid according to claim 1, wherein the neutral photosensitizer is riboflavin butyrate.

* * * * *